United States Patent
Tan et al.

(10) Patent No.: US 8,512,741 B2
(45) Date of Patent: Aug. 20, 2013

(54) ELECTROSPUN CALCIUM PHOSPHATE NANOFIBERS

(75) Inventors: Jian Tan, Ithaca, NY (US); Yong L. Joo, Ithaca, NY (US)

(73) Assignee: Cornell Research Foundations, Inc., Ithaca, NY (US)

( * ) Notice: Subject to any disclaimer, the term of this patent is extended or adjusted under 35 U.S.C. 154(b) by 746 days.

(21) Appl. No.: 12/439,398

(22) PCT Filed: Sep. 4, 2007

(86) PCT No.: PCT/US2007/077560
§ 371 (c)(1),
(2), (4) Date: Mar. 27, 2009

(87) PCT Pub. No.: WO2008/028194
PCT Pub. Date: Mar. 6, 2008

(65) Prior Publication Data
US 2009/0317446 A1    Dec. 24, 2009

Related U.S. Application Data

(60) Provisional application No. 60/824,377, filed on Sep. 1, 2006.

(51) Int. Cl.
*A61F 13/00* (2006.01)
*A61F 2/00* (2006.01)
*A61C 8/00* (2006.01)

(52) U.S. Cl.
USPC ......... 424/443; 424/422; 424/423; 433/201.1

(58) Field of Classification Search
None
See application file for complete search history.

(56) References Cited

U.S. PATENT DOCUMENTS

| 5,652,056 | A  | * | 7/1997  | Pepin         | 428/364   |
| 6,846,493 | B2 |   | 1/2005  | Pugh et al.   |           |
| 6,855,169 | B2 | * | 2/2005  | Boyer et al.  | 623/23.63 |
| 2004/0258726 | A1 |   | 12/2004 | Stupp et al. |           |

OTHER PUBLICATIONS

Biological Evaluation of Chitosan Nanofiber Membrane for Guided Bone Regeneration, Chin et al., Journal of Periodontology, Oct. 2005, vol. 76, No. 10, pp. 1778-1784.*
Carbon nanofiber—copper composite powder prepared by electrodeposition, Arai et al., electrochemistry communication, 2003.*
Ramay et al. "Biphasic calcium phosphate nanocomposite porous scaffolds for load-bearing bone tissue engineering"; Biomaterials 25 (2004) 5171-5180.*
Dorozhkin et al. "Biological and medical significance of calcium phosphates", Angrew Chem Int. Ed. 2002, 41, 3130-3146.*
Ma "Scaffold for tissue fabrication", Materialstoday, May 2004, 30-40.*

(Continued)

*Primary Examiner* — Isis Ghali
(74) *Attorney, Agent, or Firm* — Fahmi, Sellers, Embert & Davitz

(57) ABSTRACT

Calcium-phosphate nanofiber matrices comprising randomly dispersed crystalline calcium-phosphate nanofibers are provided. The nanofibers are synthesized using sol-gel methods combined with electrospinning. The nanofibers may be hollow, solid or may comprise a calcium-phosphate shell surrounding a polymer containing inner core to which biologically functional additives may be added. The nanofiber matrices may be used to culture bone and dental cells, and as implants to treat bone, dental or periodontal diseases and defects.

85 Claims, 5 Drawing Sheets

(56) References Cited

OTHER PUBLICATIONS

Instron homepage [online]. Retrieved from the Internet <URL:http://www.instron.us/wa/home/default_en.aspx>.
Micromeritics homepage [online]. Retrieved from the Internet <URL:http://www.micromeritics.com/>.
ATCC The Global Bioresource Center [online]. Retrieved from the Internet <URL:http://www.atcc.org/>.
http://www.criver.com/reasearch_models_and_services/transgenic_services/tgresearchmodels.html. Charles River [online]. Retrieved from the Internet <URL:http://www.criver.com/en-US/ProdServ/ByType/ResModOver/Pages/home2.aspx>.
Cell/Tracker TM [online]. Retrieved from the Internet <URL:http://dbkgroup.org/celltracker/>.
http://probes.invitrogen.com/servlets/publications?id=444 [online]. Retrieved from the Internet <URL:http://probes.invitrogen.com/>.
Fast Blue RR Salt and naphthol AS-MX phosphate alkaline solution. Sigma-Aldrich homepage [online]. Retrieved from the Internet <URL:http://www.sigmaaldrich.com/sigma-aldrich/home.html>.
Thermo Scientific/Pierce Protein Research Products [online]. Retrieved from the Internet <URL:http://www.piercenet.com/products/browse.cfm?fldID=020201>.
Invitrogen homepage [online]. Retrieved from the Internet <URL:http://www.invitrogen.com/site/us/en/home.html>.
International Search Report for international application No. PCT/US07/077560 issued by the International Searching Authority mailed on Aug. 28, 2008.
Written Opinion of the International Searching Authority for international application No. PCT/US07/077560 issued by the International Searching Authority mailed on Aug. 28, 2008.

* cited by examiner

ELECTROSPUN CALCIUM PHOSPHATE NANOFIBERS

CROSS-REFERENCE TO RELATED APPLICATION

This application claims priority to U.S. Prov. App. Ser. No. 60/744,023, filed on Mar. 31, 2006, the disclosure of which is hereby incorporated by reference in its entirety.

STATEMENT OF GOVERNMENT RIGHTS

This invention was made with Government support under contract number NIDCR-DE14097, awarded by the National Institutes of Health ("NIH"). The Government has certain rights in this invention.

FIELD OF INVENTION

The present invention relates to nanofibers and more particularly nanofiber matrices and nanofiber mats useful in the regeneration of bone and dental tissue.

BACKGROUND

Synthetic biomaterials have become increasingly important in biomedical applications. Calcium-based materials, for example, have been used for the restoration of bone and dental tissue function. Various crystalline phases of calcium phosphate ("Ca—P"), such as hydroxyapatite $Ca_5(PO_4)_3OH$, tricalcium phosphate ($Ca_3(PO_4)_2$, "TCP"), amorphous calcium phosphate ($Ca_3(PO_4)_2$, "ACP"), octacalcium phosphate ($Ca_8H_2(PO_4)_6 \cdot 5H_2O$, "OCP"), tetracalcium phosphate and carbonated or fluoridated apatite have been used in bone and dental implants in many forms for decades. Dense sintered hydroxyapatite has been used in middle ear implantation. Calcium phosphate cement has been used in filling bone defects in dental and orthopedic surgery. Calcium phosphate coatings on metal implants have been shown to encourage direct bone deposition on the implants, thereby forming a strong bond between implants and bone tissues.

For repair of bone defects, engineered matrices and scaffolds should not only provide mechanical support for cell growth, but should also mimic the extracellular matrix ("ECM") of the desired tissue. However, current polymeric nanofibers do not adequately mimic the natural in vivo three-dimensional morphology and environment experienced by bone and dental cells. Those polymeric nanofibers that do employ calcium phosphate do so only in the form of amorphous calcium phosphate mixed into the primarily polymer based nanofibers. Such polymeric nanofibers do not mimic the highly crystalline calcium phosphate environment experienced by bone and dental cells. Moreover, currently existing microfibers are too large to adequately mimic the ECM of the desired tissue. However, to date, matrices comprising calcium phosphate nanofibers in any crystalline phases, particularly those in randomly-dispersed fibrous networks that mimic the ECM of naturally occurring bone and/or dental cells, remain elusive. Thus, there is a continuing need to develop and improve nano-scale fibrous structures comprising primarily calcium phosphate that can be used for bone and dental tissue repair and regeneration.

SUMMARY OF INVENTION

The calcium phosphate ("Ca—P") nanofibers of the present invention comprise calcium phosphate with one or more Ca—O—P linkages, such that the phosphate group is selected from the group consisting of orthophosphate ($PO^{2-}$) ions, metaphosphate ($PO_4^{3-}$) ions, and pryophosphate ions ($P_2O_7^{4-}$), and optionally hydrogen or hydroxide ions. The nanofibers of the invention may take various forms. In one embodiment, the nanofibers comprise a continuous cross-section of crystalline calcium phosphate. In another embodiment, the nanofibers comprise a polymeric core and a crystalline calcium phosphate shell surrounding at least a portion of the core. In still another embodiment, the calcium phosphate nanofibers are hollow (i.e., nanotubes). The diameter of the nanofibers may range from between about 10.0 nm to about 2 microns, preferably between about 50.0 nm to about 500.0 nm, more preferably between about 75.0 nm to about 300.00 nm, and particularly between about 100.00 and 200.00 nm.

The nanofibers may exhibit various phases, including hydroxyapatite (HAP), tricalcium phosphate (TCP, Ca/P=1.5) tetracalcium phosphate (TTCP, Ca/P=2.0) and octacalcium phosphate (OCP, Ca/P=1.33). These compounds are typically biocompatible.

In one embodiment, the present invention is directed to 3-D nanofiber matrices, mats or scaffolds comprising randomly-dispersed Ca—P nanofibers with interstices between the nanofibers, such that the surface area of the nanofiber matrix suitably mimics the natural environment experienced by bone and dental cells in vivo, thus providing an adequate environment for bone and dental cells to grow in both in vivo and in vitro environments.

The invention is also directed to a method of making 3-D matrices of calcium-phosphate fibers in which the fibers are randomly dispersed, as well as to the synthesis of randomly dispersed calcium-phosphate core-shell nanofibers comprising a polymeric core and a calcium phosphate shell. The method comprises the steps of providing (i) a first dispersion comprising at least one polymeric substance, preferably a linear polymer with an elongational viscosity between about 1,000 poise and about 3,000 poise; (ii) providing a second dispersion comprising calcium phosphate; (iii) placing the first dispersion in an inner tube and the second dispersion in an outer tube of a co-axial syringe; and (iv) subjecting the dispersion to co-axial electrospinning to collect a plurality of nanofibers, such that the nanofibers form a nanofiber matrix of randomly dispersed nanofibers. In some embodiments, the polymeric core is further seeded with functional biological additives such as growth factors, cytokines, therapeutic peptides/proteins, etc., to aid in bone or dental repair or regeneration.

The calcium phosphate nanofiber matrices may be used for various purposes, including use as cell culture systems, cell carriers, and the repair of various body parts and organs, such as bone and dental tissue repair/regeneration and skin grafts.

BRIEF DESCRIPTION OF THE DRAWINGS

Certain embodiments of the present invention are illustrated by the accompanying figures. It should be understood that the figures are not necessarily to scale and that details not necessary for an understanding of the invention or that render other details difficult to perceive may be omitted. It should be understood, of course, that the invention is not necessarily limited to the particular embodiments illustrated herein.

DETAILED DESCRIPTION

Figure 1:
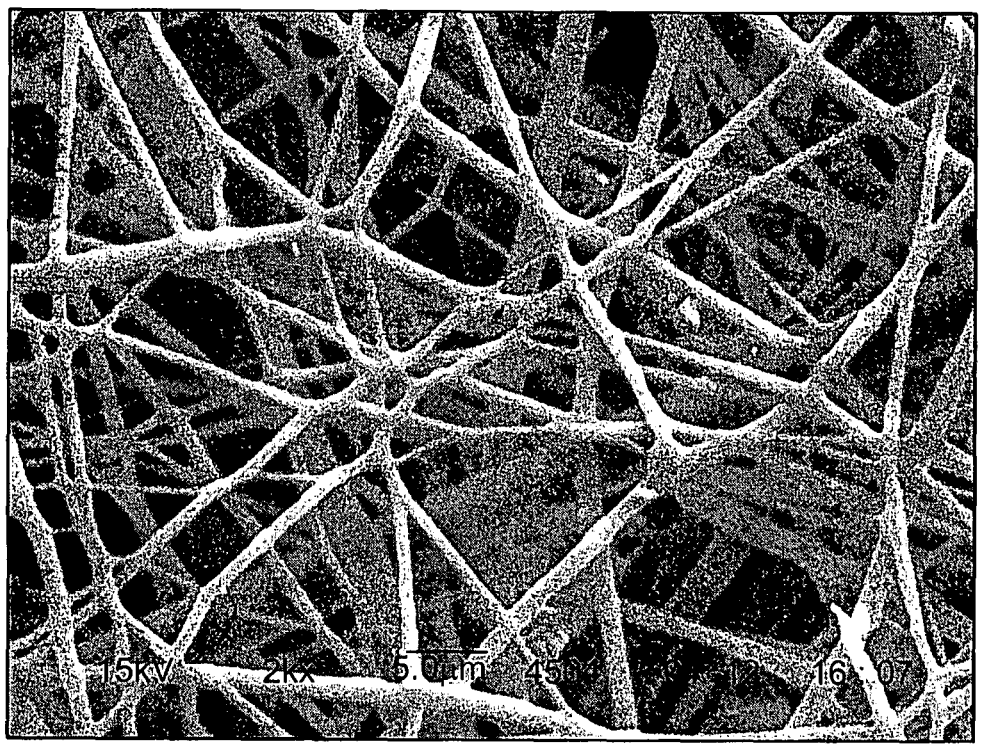
FIG. 1 is a scanning electron microscope ("SEM") image of a nanofiber mat made in accordance with one embodiment of the present invention.

Non-woven nanofibers of the present invention comprise a plurality of repeating calcium phosphate units. In certain embodiments, the nanofibers comprise substantially non-derivatized calcium phosphate (i.e., the chemical structure of the calcium phosphate is void of other elements, compounds and substances except for impurities). In other embodiments of the invention, the calcium phosphate is either substantially crystalline, or amorphous with some crystalline structure. The term calcium phosphate, as used herein, means the family of compounds containing calcium ions ($Ca^{2+}$) together with at least one of orthophosphate ions ($PO^{2-}$), metaphosphate ions ($PO_4^{3}$), or pryophosphate ions ($P_2O_7^{4-}$), and optionally hydrogen or hydroxide ions, having one or more Ca—O—P linkages. Examples include tricalcium phosphate $Ca_3(PO_4)_2$ (also called tribasic calcium phosphate, occurring in alpha and beta phases), dicalcium phosphate $CaHPO_4$ (also called calcium monohydrogen phosphate), calcium dihydrogen phosphate $Ca(H_2PO_4)_2$ (also called monocalcium phosphate) and hydroxyapatite $Ca_{10}(PO_4)_6(OH)_2$. A scanning electron microscope image of a plurality of nanofibers according to one embodiment of the present invention is shown in FIG. 1. When the plurality of nanofibers is randomly dispersed, with at least some of the nanofibers in physical contact with one another, a nanofiber matrix, or mat, is formed. The nanofiber mat may contain interstices, gaps or pores between the nanofibers.

The nanofibers may also comprise a polymer binder. The polymer binder may include linear aliphatic polymers often used in tissue engineering including poly(glycolic acid) ("PGA"), poly(lactic) acid ("PLA," which by virtue of the extra methyl group in its repeating unit is more hydrophobic than PGA), and their copolymers such as poly(lactic acid-co-glycolic acid) ("PLGA"). The properties of the PLGAs may be varied by altering the ratio of lactic acids to glycolic acids. These polymers (PLA, PGA, and PLGAs) are also preferred as they have been approved by the U.S. Food and Drug Administration ("FDA") for human clinical applications.

Other biocompatible linear aliphatic polymers include polyethers such as polyethylene glycol ("PEG"), polyethylene oxide ("PEO"), polypropylene oxide ("PEP") and their co-polymers, for instance, poly(ethylene glycol-co-propylene oxide) ("PEG-PPO"). Suitable polymer binders also include poly(-caprolactone) ("PCL"), poly(hydroxy butyrate) ("PHB") and their respective copolymers. In another embodiment, biodegradable polymers including poly (propylene fumarate) ("PPF"), tyrosine-derived polymers, segmented polyurethane-based polymers, polyphosphoesters, polyphosphazenes, polyanhydrides and poly(ortho esters) may be used as polymer binders. In another embodiment, the polymer binder may be a water-soluble vinyl polymer. Water-soluble vinyl polymers include polyvinyl alcohol ("PVA"), polyvinyl ether and polyvinyl pyrrolidone. In yet another embodiment, block co-polymers comprising combinations of two or more of any of the aforementioned polymers may be used.

In one embodiment, the nanofiber may be solid when seen in any cross-section to the longitudinal axis of the nanofiber, such that the nanofiber comprises a continuous cross-section of calcium phosphate. The cross-section may be taken along a perpendicular axis. In another embodiment, the nanofiber may comprise a calcium phosphate shell surrounding a hollow core. In yet another embodiment, the calcium phosphate shell surrounds a solid core having at least one polymeric substance. The polymeric substance present in the core may comprise one or more biodegradable polymers, alone or in combination with other functional additives.

The calcium phosphate nanofibers exhibit various advantageous properties, cross-sectional distances (or diameters when the cross-section of the nanofibers closely approximates a circle) in the nanometer range, a three-dimensional network structure, and interconnected porosity. The nanofibers are relatively thin, comprising cross-sectional dimensions ranging in size from about 10.0 nm to about 2.0 microns when cut or viewed in cross section which may be taken perpendicular to the longitudinal axis of the fiber. In another embodiment, the cross-sectional dimensions may range from about 50.0 nm to about 500.0 nm, while in a third embodiment, the cross sectional dimensions range from about 75.0 nm to about 300.0 nm. In a fourth embodiment, the cross sectional dimensions of the nanofiber are from about 100.0 nm to about 200.0 nm. In those instances, where the cross-section of the fiber approximates a circle, the cross-sectional dimension is the diameter of the circle. In other instances where the cross-section is irregularly-shaped, the cross-sectional dimension is the maximum cross-sectional distance between any two points on the surface of the nanofiber taken on a cross-section perpendicular to the longitudinal axis of the nanofiber.

Fiber cross-sectional distances, such as fiber diameters, are measured using scanning electron microscopy (e.g., Zeiss Supra or Ultra SEM with a resolution of 1 nm). In order to directly probe the Ca—P crystals with 1.0 nm resolution in nanofibers, elemental mapping on an Energy Filtering Transmission Electron Microscope ("EFTEM") using electron energy loss spectroscopy ("EELS") is utilized. The surface charge of the nanofibers is typically neutral to net positive, as determined by zeta potential testing The nanofibers may possess a plurality of internal pores. The dimensions of the pore range from about 0.1 nm to about 10.0 nm. In another embodiment, the size of internal pore ranges from about 2.0 nm to about 5.0 nm. In one embodiment of the invention, a plurality of internal pores may interconnected.

As previously stated, the nanofibers may exhibit various phases, including hydroxyapatite ("HAP"), tricalcium phosphate ("TCP," Ca/P=1.5 (molar ratio "m/m")), tetracalcium phosphate ("TTCP," Ca/P=2.0 (m/m)) and octacalcium phosphate ("OCP," Ca/P=1.33 (m/m)). The crystal habit of these compounds ranges from monoclinic to triclinic to hexagonal. X-ray diffraction ("XRD") is used to probe the presence of calcium phosphate crystals and determine structural characterization to compare with standard calcium phosphate phases such as HAP, OCP, TCP, etc. The degree of crystallinity may be at least about 40% and preferably between about 70% and 99%, the non-crystalline calcium phosphate being amorphous. The degree of crystallinity can be determined by XRD, calorimetry, density measurements or infrared spectroscopy.

The mechanical strength of nanofibers may also be characterized. Tensile strength and compressive strength may be between about 25.0 and 1,000.0 MPa (millipascal). Tensile experiments of bulk nanofiber mats are carried out on a conventional Instron 1125 test system (www.instron.com), while the modulus and yield strength of a single Ca—P nanofiber may be measured by depressing the suspended nanofiber with a tip of an Atomic Force Microscope.

A plurality of nanofibers, randomly dispersed, may take the form of a three-dimensional nanofiber matrix. Such a matrix may alternatively be termed a scaffold or a mat. When the nanofibers take the form of a nanofiber mat, the mat may exhibit a relatively high specific surface area, owing to relatively small nanofiber diameters and the presence of porosity as a result of pore-like interstices within the nanofiber mat. The specific surface area of the nanofiber mat, measured with a Micrometrics Phys/Chemi Sorption Analyzer (http://www.micromeritics.com/), is typically greater than about 10 $m^2/g$ and more particularly between about 100 $m^2/g$ and 1,200 $m^2/g$ or 600 $m^2/g$ and 1,100 $m^2/g$, and still more particularly between about 800 $m^2/g$ and about 1,000 $m^2/g$. The nanofiber mat may include inter-fiber pores. Such pores within the mat are defined by the tiny interstices or gaps between the randomly dispersed nanofibers of the mat. The size of the pores between the randomly-dispersed nanofibers range from about 0.5 microns to about 50.0 microns, more particularly between about 1.0 micron to about 10.0 microns and may be measured using scanning electron microscopy.

To make the nanofibers of the present invention, various processes may be employed. In one embodiment, calcium phosphate nanofibers may be made by electrospinning a sol-gel precursor comprising calcium phosphate and a polymer binder, followed by optional calcination, a thermal treatment process by which a volatile fraction, such as a polymer binder, water or solvent may be removed. In another embodiment, nanofibers may be made by the same process without the use of a polymer binder. Additionally, nanofibers comprising a calcium phosphate skin layer (or shell) and a biodegradable polymeric core may be made by employing co-axial electrospinning.

The goal of the sol-gel synthesis is to preferably yield a reaction product comprising a relatively high elongational viscosity, for example between about 10.0 poise to about 1,000.0 poise. If the solution viscosity is too low, either beads of solution will form on the fibers or only discontinuous jets via the electrospinning mechanism will be formed. If the viscosity of the solution is too high, fiber yield may be compromised. Preferably, the solution viscosity is between about 10.0 poise and 1000.0 poise, more particularly between about 200.0 poise to about 600.0 poise.

Figure 4:
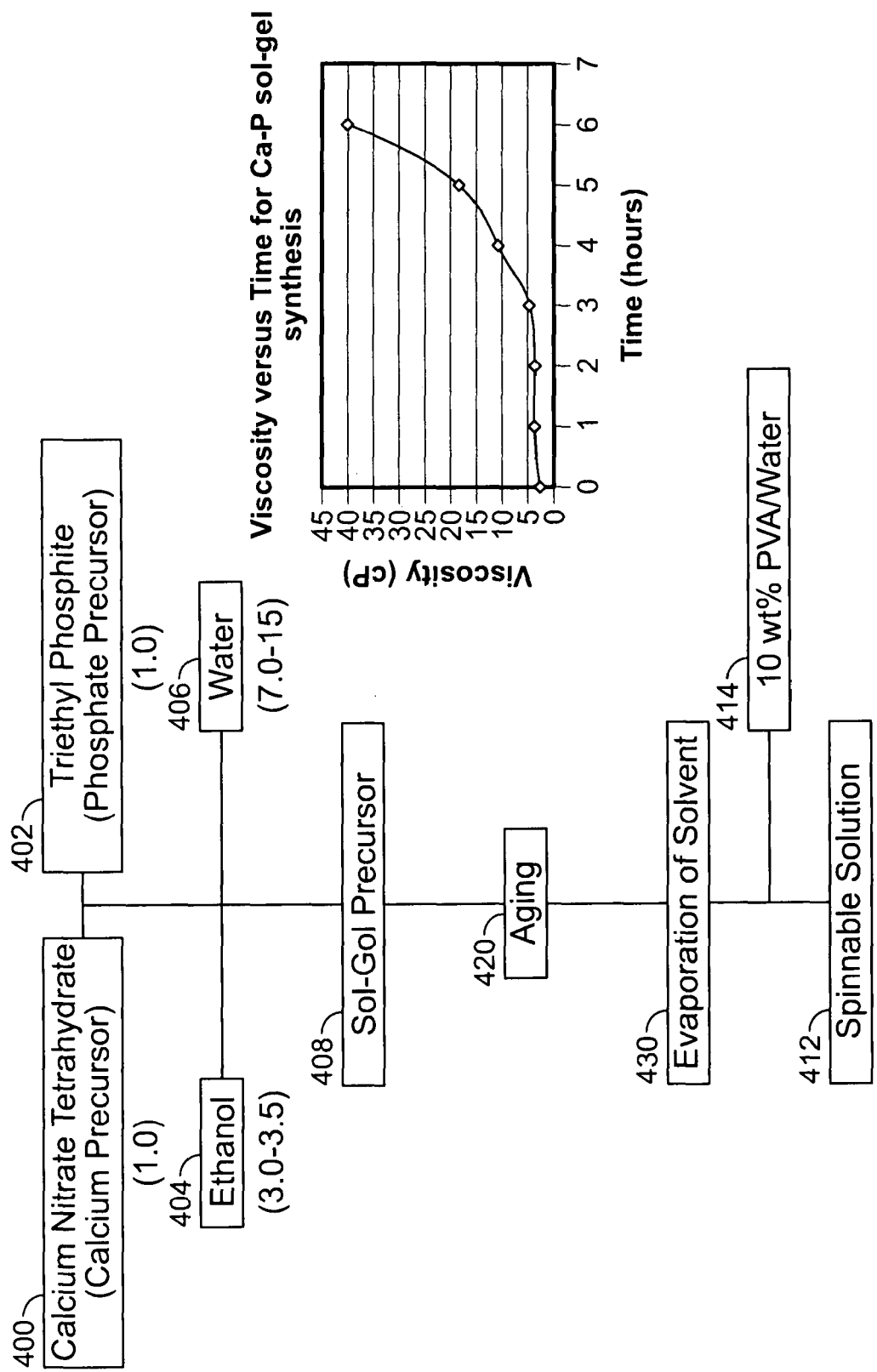
FIG. 4 illustrates a flow-chart of the general parameters for the sol-gel process of the present invention with an accompanying viscosity curve.

A schematic of the sol-gel synthesis is shown in FIG. 4. To carry out the sol-gel synthesis, calcium and phosphorous based starting materials are combined. Suitable calcium-based starting materials include, but are not limited to, materials comprising calcium nitrate, calcium acetate, calcium ethoxide and calcium glycolate; suitable phosphate-based starting materials include, but are not limited to, materials comprising triethyl phosphate, and various phosphate.

An illustrative embodiment for synthesis of Ca—P sol-gel precursor as shown in FIG. 4 involves triethyl phosphate 402 and calcium nitrate tetrahydrate 400. This synthesis begins with the addition of triethyl phosphate 402 to anhydrous ethanol 404 in a vial. Distilled water 406 is then added and the solution is allowed to hydrolyze for at least about 1.0 hour with vigorous stirring. Calcium nitrate tetrahydrate 400 dissolved in anhydrous ethanol 404 is added dropwise to the triethyl phosphate solution while stirring to form the sol-gel precursor 408. To achieve the appropriate elongational viscosity, the molar ratio of starting material to solvent to water to catalyst may be adjusted. When the solvent used is ethanol, the molar ratios of Ca:P:water:ethanol may be about 1.67:1: 3-6.5:7.4-14.8, with a preferred ratio of 1.67:1:6.5:14.8. An aging process 420 follows in which the solution is aged for at least about 16.0 hours and more particularly between 16.0 hours and 72.0 hours. After aging, an evaporation process 430 follows, in which the solvents are evaporated at temperatures ranging from 25° C. to about 80° C. for about 6.0 hours to obtain a clear viscous spinnable liquid 412. A solution of 10% by weight of a polymer binder and water 414 is optionally mixed with the calcium phosphate solution in a volumetric ratio of about 9:1 or 8:2, 7:3 and 6:4. The polymer binder may be polyvinyl alcohol ("PVA") or polyglycolic acid. After evaporation of solvents at 80° C., the calcium phosphate sol is stirred for about an hour to obtain a relatively homogeneous mixture.

The sol-gel synthesis of calcium phosphate proceeds as follows:

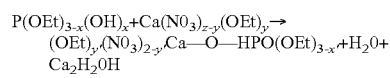

Figure 2:
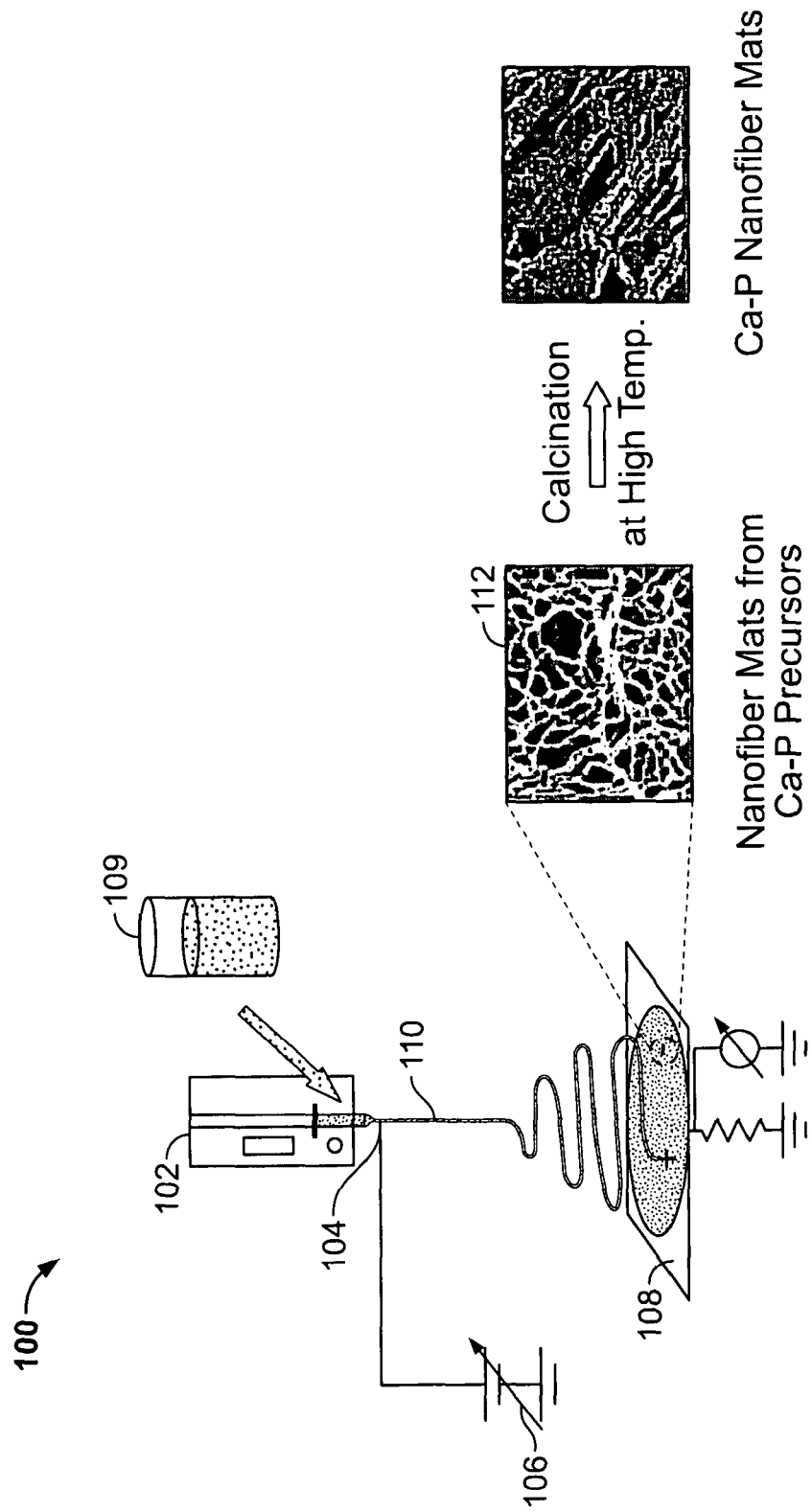
FIG. 2 is a perspective view of an electrospinning apparatus used to prepare the nanofibers of the present invention.

Hydrolyzed phosphorus sol in the form of phosphoric ester $P(OEt)_{3-x}(OH)_x$ with Ca in the form of $Ca(NO3)_{z-y}(OEt)_y$ in anhydrous ethanol may be used to form Ca—P sol comprising oligomeric derivatives linked by Ca-0-P bonds. Ca-0-P bonds provide a linear structure suitable for obtaining fibers via electrospinning. The schematic of the calcium phosphate nanofiber scaffold fabrication via electrospinning is shown in FIG. 2. The ratio of water, ethanol, calcium, and phosphorous can be varied to produce fibers with desirable features. It is understood that determination of the ratios may be made by one of ordinary skill in the art without undue experimentation. PVA may be added to the Ca—P sol-gel precursor to enhance processability and to aid in the production of substantially continuous fibers.

The ultimate reaction product of the sol-gel synthesis may, thus, comprise a linear polymer with the general formula F:

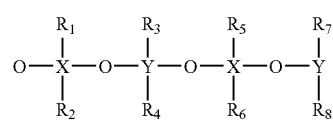

Wherein X=calcium Ca, Y=phosphorus, P and $R_1$-$R_8$≠oxygen bonded to another one of X or Y. Typically, $R_1$-$R_8$=$OCH_2CH_3$. Such a configuration helps optimize nanofiber formation during the electrospinning step, avoiding unwanted break-down or disintegration of material. The molecular weight of the linear polymer is typically between about 10,000 amu and 300,000 amu and more particularly between about 100,000 amu to 200,000 amu. The control of elongational viscosity in electrospinning is more important than in conventional spinning because of higher elongational deformation during electrospinning.

In the event co-axial electrospinning of a calcium phosphate shell on a chemically distinct polymeric core is desired, other types of sol-gel synthesis may be employed to produce a sol-gel precursor to the polymeric core. Virtually any immiscible polymer that does not react or dissolve in ethanol may be employed in the polymeric core. Pyridine, polylactic co-glycolic acid and tetraethyl orthosilicate ("TEOS") are just some suitable examples.

A sol-gel synthesis reaction using TEOS as a precursor is illustrative. TEOS is added to a solvent of ethanol and water, followed by the dropwise addition of a catalyst (for example, a solution of hydrochloric acid in water), with vigorous stirring. In one embodiment, the molar ratios of TEOS:EtOH:H20:HCL are about 1:2:2:0.01. Although organic polymeric binders, such as PVA may be employed, the reaction may proceed without the use of such binders. The solution is heated for one to three hours at a temperature of about 50° C. The aforementioned steps yields a dispersion comprising at least one linear chain with the general formula:

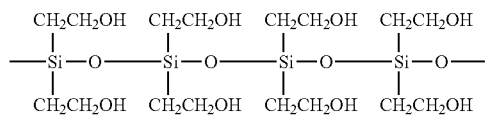

Various additives may also be incorporated into the above-described sol-gel precursor. In one embodiment, such additives include compounds that improve cell function and mechanical strength of the electrospun fibers, for instance, compounds containing carbonate and fluoride ions to make carbonated or fluorinated apatite. Compounds containing these ions are typically added to the sol, with fluoride added in an amount less than about 5.0 wt. %, whereas carbonate may be added in an amount less than about 20.0 wt. %. Other additives, such as compounds comprising Sr, Mg, Mn, Zn, Na and K, may also be employed. Additionally, biologically active molecules, such as proteins, peptides, DNA, RNA, antibiotics, antimicrobials, anti-inflammatories, steroids and chemotherapeutical agents. Examples include osteogenic factors, neurotrophic factors, angiogenic factors, bone morphogenic protein ("BMP"), transforming growth factors ("TGF"), vascular endothelial growth factor ("VEGF"), platelet-derived growth factor ("PDGF"), neurotrophins, cytokines, etc. The presence of these materials in the sol yields a co-axially electrospun core comprising these same advantageous materials. Biphasic calcium phosphate ceramics are also possible through the methods of the present invention.

After the sol-gel step and recovery of the dispersion comprising linear chains, the dispersion is subjected to electrospinning. Electrospinning is a fiber formation process that relies on electrical, rather than mechanical forces to form thin fibers with diameters ranging between about 50.0 nm and about 10.0 microns. A strong electric field is used to draw a solution from the tip of a capillary to a grounded collector. The electric field causes a pendant droplet of the solution at the capillary tip to deform into a conical shape. When the electrical force at the surface of the tip overcomes the surface tension of the solution, a charged jet is ejected. The jet moves toward the collector plate, which acts as a counter electrode. The solvent begins to evaporate after jet formation, causing the deposit of a thin fiber on the collector. To the extent any solvent remains, the fibers may be heated at temperatures of about 150° C. to remove residual solvent.

Referring now to FIG. 2, one embodiment of an electrospinning apparatus 100 for use with the present invention is illustrated. Apparatus 100 comprises syringe 102, comprising an inner diameter of between about 0.20 millimeters to about 0.60 millimeters, tip 104, high voltage supplier 106 positioned at or near tip 104, and collection plate 108, constructed of a conductive material, such as aluminum, stainless steel, or a surface oxidized silicon. The diameter of nanofibers may be decreased by decreasing the inner diameter of syringe 102. The distance between tip 104 and collector 108 is about 10.5 centimeters. High voltage supplier 106 includes a voltage of about 20 kV. Collector 108 is grounded to create an electric field difference between tip 104 and collector 108, causing jet 110 to move from the high electric field at tip 104, to grounded collector 108. Collector 108 may also be a rotating collector.

Once apparatus 100 is assembled, dispersion 109 created during the sol-gel synthesis step is placed into syringe 102, and pumped through at a relatively constant flow rate of about 0.03 mL per minute. As pumping continues, charged jet 110 is ejected and elongates as it moves towards collector 108. Thus, a plurality of randomly oriented non-woven ultra-thin fibers or nanofibers 112 are collected on collector 108. At this point, the nanofibers 112 comprise a three-dimensional network of calcium phosphate.

Figure 3:
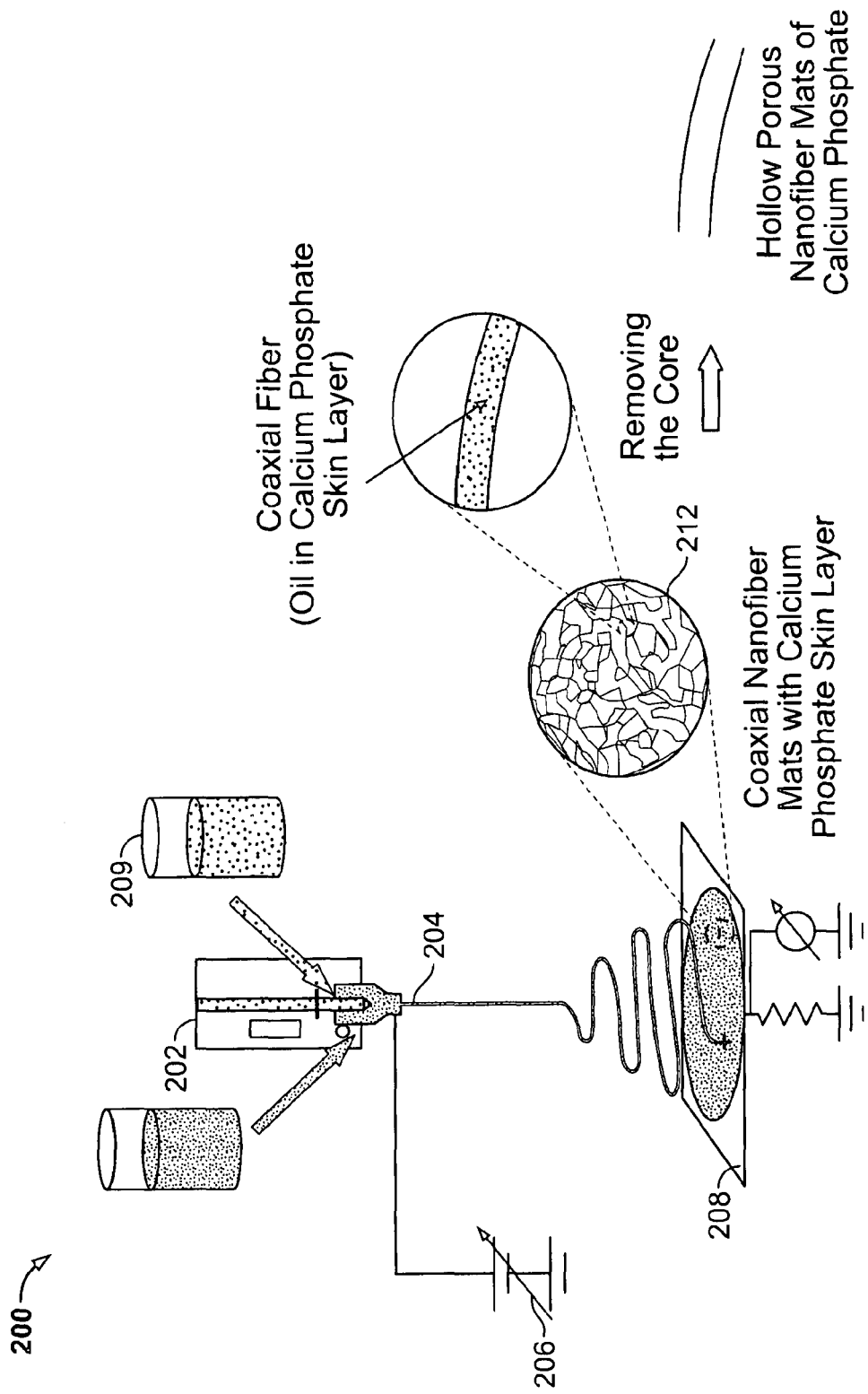
FIG. 3 is a perspective view of an alternate setup of the electrospinning apparatus of FIG. 2, adapted for co-axial electrospinning.

In an another embodiment, shown in FIG. 3, co-axial electrospinning may be employed. In co-axial electrospinning, a dual syringe pump with controlled flow rates of both inner and outer solutions is used.

Co-axial electrospinning apparatus 200 comprises dual syringe 202 which comprises an internal tube positioned within an external tube, tip 204, high voltage supplier 206 and collector 208 for receiving nanofibers 212. Under this construction an internal jet with an external jet is ejected from the syringe; the internal jet may comprise polymeric substances such as those prepared from TEOS, while the external jet comprises the calcium phosphate dispersion 209, prepared during sol-gel synthesis.

Alternatively, the sol-gel dispersion may be subjected to conventional mechanical spinning using an extruder, die and winder. Conventional spinning employs a mechanical force to draw fibers out of solution and yields fiber diameters between about 3.0 microns and about 5.0 microns.

After electrospinning, the polymeric binder may be removed from the fibers through calcination. Calcination involves heating to relatively high temperatures. The calcination temperature and time depend upon the materials being used as well as the needs of the user. The typical temperature ranges from 500° C. to about 1,200° C. and more particularly from about 600° C. to about 800° C. Calcination is typically carried out anywhere between two and twelve hours and more particularly between about five to seven hours. Through the calcination process, the polymer binder is effectively removed and the resulting fibers comprise essentially calcium phosphate.

Calcination also impacts several properties of the nanofibers. Calcination can decrease nanofiber diameters and internal porosity and transform amorphous materials into crystals. Higher temperatures produce nanofibers with smaller diameters. In addition, extended calcination typically decreases and ultimately removes the internal porosity of the fibers. Provided calcination does not proceed too far, the collective nanofibers themselves (as opposed to the mat) may comprise a plurality of internal pores, at least one of which exhibits a diameter between about 0.1 nm and about 10.0 nm and more particularly between about 2.0 nm and about 5.0 nm.

If co-axial electrospinning is employed, the calcining step may be eliminated, or its duration and/or temperature may be reduced, as calcination may lead to removal of the polymeric core. In order to maintain the presence of the core, therefore, the collected nanofibers are preferably not exposed to calcination temperatures for extended periods. Such co-axial electrospinning, however, may rely on the presence of various polymer binders added to the Ca—P sol, such as polylactide, poly(D,L-lactide-co-glycolidepolylactide) and/or polycaprolactone in methylene chloride. In order to remove the polymer binders while leaving the polymeric cores intact, calcination may be controlled by changing the temperatures and time of calcination.

The final product generated by the above-described three step process is a nanofiber mat comprising a plurality of nanofibers comprising non-derivatized crystalline calcium phosphate. Some nanofibers within the mat may be adhered to one another, based on the presence of residual solvent. The nanofibers may comprise a three-dimensional network. To increase crystal content on external surfaces, the fibers may be placed in water for 0.5 hours to about 1 hour prior to calcination. This step drives a hydrolysis reaction, which ultimately increases crystal growth by between about 15% to about 50% of the original coverage.

The calcium phosphate nanofibers may be used for various purposes, including repair of various body parts and organs, such as bone and dental tissue repair/regeneration and skin grafts. For example, calcium phosphate nanofiber mats be implanted during surgery or electrospun onto the surface of a soft tendon tissue so that the tendon can directly connect with hard bone to reconstruct an injured ligament implanted during surgery. The calcium phosphate fibers also have potential applications in dental tissue repair and regeneration (in particular guide tissue regeneration ("GTR")) of dental structures, such as dental tissues, damaged by dental or periodontal diseases. The calcium phosphate fibers also have potential applications in repair and regeneration (in particular guide tissue regeneration ("GTR")) of bone tissues, damaged by injury, disease or as a result of genetically-based bone defects. To this effect, the calcium-phosphate nanofiber mats assist in bone/dental tissue engineering by serving as cell carriers. In such instances, the calcium-phosphate fiber mats are used as bone or dental implants in which the mats are cultured with the necessary bone or dental cells, respectively, in vitro such that the cells adhere to the mat and reach tissue-like densities, and then implanted adjacent to the damaged or diseased bone or dental tissue, or to fill bone and dental tissue defects. Such bone and dental cells include osteoblast and odontoblast cells respectively. The fibers are also useful in reconstructing an injured ligament in between hard bone and soft tendon tissue, by implanting the nanofiber matrix onto the surface of the soft tendon tissue and adjacent to the injured ligament such that adjacent bone and tissue can proliferate on the matrix, allowing the tendon to connect to the hard bone.

Figure 5:
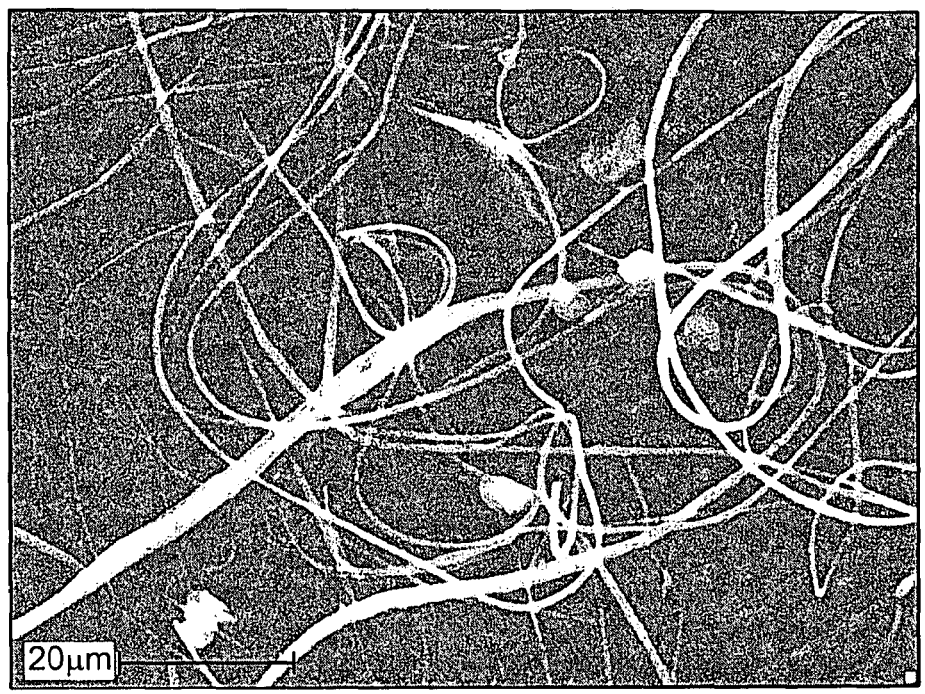
FIG. 5 illustrates the growth of osteoblast-like Saos-2 (Saos-2) cells on a nanofiber mat comprising co-axial fibers made in accordance with one embodiment of the present invention. The fibers comprised a silica core and a calcium phosphate shell.
Figure 6:
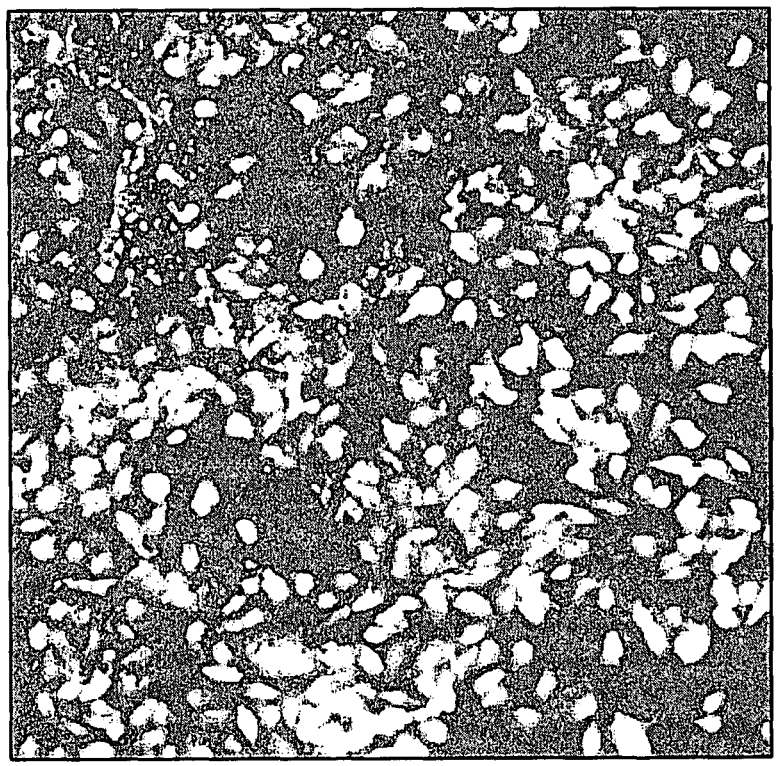
FIG. 6 illustrates live DPM cells stained with fluorescence to show that about 90% of the cells were alive after a week-long culture on the nanofiber mat of the present invention.

As the cells show microstructure dependent behavior, it is believed that adhesion, proliferation and differentiation of the cells is significantly improved through use of the present invention. The fiber network call be seeded or cultured with such cells before implantation. SEM images of co-axially electrospun fibers, comprising a silica core and a calcium phosphate shell, are shown in FIG. 5. These fibers were seeded with Saos-2 cells, which penetrated the fiber network and exhibited a substantially round morphology similar to the these types of cells in vivo. As shown in FIGS. 5 and 6, these cells grow well in the presence of the nanofibers of the present invention.

Additionally, core-shell nanofibers are useful for the delivery of biofunctional molecules such as growth factors to enhance guide tissue regeneration. Core-shell fibers therefore enable a novel method of delivery of biofunctional molecules.

The present invention is illustrated, but in no way limited by the following examples.

EXAMPLES

In Examples 1 (a) and 1 (b), calcium phosphate nanofiber mats were generated using sol-gel synthesis with a polymer binder, followed by electrospinning and calcination.

Example 1(a)

Triethyl phosphite and calcium nitrate were selected as phosphate and calcium precursors for nanofiber synthesis of hydroxyapatite nanofibers. To produce such fibers, a molar ratio of calcium to phosphate of 1.67:1 was desirable. The resulting Ca:P:water:ethanol mole ratio for this study was 1.67:1:6.5:14.8. Triethyl phosphite $(ETO)_3P$ (MP Biomedicals) was added to 2.0 mL of 200-proof ethanol in a small vial. Distilled water in an amount of 1.35 mL was subsequently added to maintain a 3.0 M phosphorus precursor solution. The phosphite solution was then allowed to hydrolyze for 1 hour at room temperature with vigorous stirring. In a separate small vial, calcium solution was prepared by dissolving 4.935 g of calcium nitrate tetrahydrate $Ca(NO_3)_2.4H_2O$ (J. T. Baker) in 7 mL of 200-proof. Dissolution of the calcium compound was facilitated by vigorous stirring at room temperature for 30 minutes. The final volume was approximately 7.5 mL. Upon completion of the phosphite hydrolysis, a stoichiometric amount of the calcium nitrate solution was added dropwise into the hydrolyzed phosphite sol. Vigorous stirring was continued for 15 minutes to obtain a clear solution that was left to age at room temperature for at least 16 hours prior to use.

A polyvinyl alcohol (PVA, Polyscience, Inc., MW 78,000, 88 mole % hydrolyzed) solution was also prepared for incorporation into the calcium phosphate solution as a polymer binder. Initially, a 10% w/v PVA/water solution was prepared by addition of polyvinyl alcohol to water. This solution was stirred, covered, at room temperature (about 25° C.) until the majority of the PVA dissolved. The solution was then heated to 80° C. and stirred for an additional 30-60 minutes until all remaining PVA particles dissolved. The final $1.425*10^{-3}$ M PVA solution was clear, viscous, and easily spinnable.

A 4:6 volumetric ratio Ca—P sol-gel precursor/PVA solution was prepared prior to electrospinning by adding 10% w/v PVA to the Ca—P sol dropwise under vigorous stirring. In order to achieve a viscosity suitable for electrospinning, this solution was then stirred open to ambient air for at least 24 hours to evaporate volatile solvents. The sol-gel precursor was allowed to settle for at least 24 hours to achieve the best spinning results.

The electrospinning conditions employed were as follows: distance from tip to collector=0.127 meters, Q=0.001 mL/min, Voltage=19-20 kV, time=2 hours. The as-spun fibers were transferred to a 50° C. thermal convection oven and stored for at least 48 hours to facilitate solvent evaporation prior to calcination. Solvent evaporation during this step allowed formation of intact fiber mats; as-spun fibers that were calcined without adequate solvent removal tended to merge together into films upon exposure to ambient air.

The as-spun fiber samples were placed in a ceramic boat and calcined in a box furnace in air. The calcination temperature was chose to: 1) promote hydroxyapatite formation from the calcium phosphate precursors (hydroxyapatite was shown to form from this Ca—P sol-gel precursor at temperatures at and above 350° C.) and 2) completely remove the polymer binder, PVA, from the fiber sample. The calcination conditions employed were: ramp rate=800° C./hour; calcination temperature=400° C.; duration=3 hours; rate of decrease in temperature=2000° C./hour; and final temperature=room temperature.

Example 1(b)

In Example 1 (b), various polymeric core/Ca—P shell nanofibers were produced by electrospinning different sol-gel precursor solutions through a spinneret comprised of two coaxial capillaries. These nanofibers included:

Type 1. Shell: non-derivatized calcium phosphate
Core: silica-containing polymeric substance
Type 2. Shell: calcium phosphate+PVA
Core: silica-containing polymeric substance
Type 3. Shell: silica-containing polymeric substance
Core: non-derivatized calcium phosphate In all cases, the core (inner solution) and shell (outer solution) solutions for electrospinning were sol-gel precursors of the respective materials. During electrospinning, the solvent began to evaporate from both solutions, thus promoting the transition from the sol to gel state. Calcination of as-spun fibers was performed in order to produce fibers as well as to obtain the desired hydroxyapatitic crystalline structure.

Silica was chosen as a material for both core and shell because of the ease of its preparation via the sol-gel method and also because of the ease of its electrospinning. It was thought that the sol-gel transition of silica sol-gel precursor during electrospinning could be harnessed to drive the formation of the calcium component of the coaxial nanofibers.

The silica sol was prepared from tetraethyl orthosilicate ("TEOS"), distilled water, ethanol, and hydrochloric acid in a molar ratio of about 1:2:2:0.01. First, TEOS was combined with ethanol in a beaker. The HCl water solution was then added dropwise to the TEOS/ethanol mixture under vigorous stirring to obtain a clear, immiscible sol. This solution was placed in a 50° C. thermal convection oven for 4-5 hours; solvent evaporation during this time period produced a clear sol with a viscosity suitable for electrospinning.

The calcium phosphate sol was prepared as outlined in Example 1 (a). In Type 1 and 3 fibers, this sol was evaporated to a viscosity suitable for electrospinning under vigorous stirring at 80° C.; evaporation times varied depending on the surface area of sol exposed to ambient conditions. In Type 2 fibers, a 4:6 volumetric ratio calcium phosphate sol-gel precursor/PVA solution was prepared prior to electrospinning by adding 10 wt. % PVA to the calcium phosphate sol dropwise under vigorous stirring. In order to achieve a viscosity suitable for electrospinning, this solution was then stirred open to ambient air for at least 24 hours to evaporate volatile solvents. The Ca—P/PVA sol-gel precursor was allowed to settle for at least 24 hours to achieve the best electrospinning results.

Co-axial electrospinning was carried out under the following conditions

|  | Type 1 Shell: pure Ca—P Core: silica | Type 2 Shell: Ca—P/PVA Core: silica | Type 3 Shell: silica Core: Ca—P |
| --- | --- | --- | --- |
| TCD* (in.) | 4-6 | 5 | 5 |
| $Q_{in}$ (mL/min) | 0.02-0.03 | 0.02 | 0.02 |
| $Q_{out}$ (mL/min) | 0.002-0.005 | 0.005 | 0.005 |
| v (kV) | 20 | 23 | 23 |
| t (hr) | 2 | 2 | 2 |

TCD = tip-to-collector distance
$Q_{in}$ = volumetric flowrate of core solution
$Q_{out}$ = volumetric flowrate of shell solution
V = voltage
t = duration of electrospinning As-spun fibers were stored in a 50° C. thermal convection oven to promote solvent evaporation prior to calcination.

The as-spun fibers were placed in a ceramic boat and calcined in a box furnace in air. The calcination temperature was chosen primarily to promote hydroxyapatite formation from the calcium-phosphate precursors (hydroxyapatite was shown to form from this sol-gel precursor at temperatures at and above 350° C. In Type 2 fibers, calcination also allowed removal of the polymer binder, PVA, from the fiber sample. The calcination conditions were the sane as those described above in connection with Example 1 (a).

Example 2

The stability and resorbability of the nanofibers of the invention in cell culture medium was studied to determine if the nano fibers undergo physical and chemical modification in a cell culture medium. The stability (or resorbability) of the nanofibers in the medium is studied first without the cells. Nanofibers were removed from the medium at various time points and observed using XRD and SEM for structural changes. The information is helpful to understand cell behavior; to determine the ratio of the rate of cell differentiation to cell proliferation; to evaluate protein adsorption, membrane receptor/ligand interactions, cytoskeleton organization and subsequent signal transduction; and to correlate in vitro studies to animal models.

To test biocompatibility and obtain optimal structures for in vivo evaluation of the fibrous structures in bone and dental tissue regeneration, the influence of the following parameters on bone and dental cell behavior were also investigated: chemical composition (Ca/P ratio), crystalline structure, crystallinity, fiber diameter, pore size, stability and mechanical strength.

Two model cell lines were used for an in vitro test of biocompatibility: osteoblast-like Saos-2 and dental papillae mesenchyme ("DPM") cells (www.atcc.org), an immortal odontogenic cell line. Saos-2 cells possess osteoblastic characteristics and were used as model cells to test compatibility with the nanofibers for bone regeneration and dental repair, especially when used as a coating of dental metal implants or as a membrane for guide tissue regeneration of periodontal and dental tissues (periodontal membrane, alveolar-bone, cementium and dentin) weakened or damaged by related diseases. DPM cells derived from Immortomouse, a transgenic mouse harboring the SV40 strain A58 early region coding sequences under the control of the mouse MHC H-2Kb class I promoter (http://www.criver.com/research_models_and_services/transgenic_services/tgre-searchmodels.html), are used. These transgenic mice (H-2Kb-tsA58) have the potential of producing cell lines derived from many different tissues. For example, periodontal ligament ("PL"), oral epithelial ("OE"), odontoblast-like and osteoblast cell lines have been successfully isolated from Immortomouse by others and provide convenient model systems for the studies in dental tissue engineering.

Prior to seeding the nanofibers with the cells, squares were cut from the calcium phosphate nanofiber mat, and sterilized by ultraviolet irradiation for 1 hour per side in a laminar hood. Alternatively, the fibers were direct spun onto glass cover slips rendering cutting unnecessary. The fibers were pre-soaked with cell-culture medium in a tissue culture plate before seeding. The fibers settled to the bottom of the plate and got wet easily. The morphology of cells was then examined by a variety of microscopy techniques including direct phase contrast visualization of live cells. In those instances where visible light could not penetrate the mineralized substrates, fluorescence-labeling of cells was employed with a Cell/Tracker™ green probe followed by observation using epi-fluorescence and confocal microscopy (http://dbk-group.org/celltracker/). In addition, cells were observed for their interactions with the substrate materials by electron microscopy. Briefly, cells on the surfaces were fixed with 2% glutaraldehyde in PBS for 2 hours at room temperature. After fixation, the samples were rinsed with phosphate buffered saline ("PBS") before dehydration with a series of graded ethanol solutions (10, 25, 50, 70, 95 and 100%). The cells were dried with a critical point dryer. The resulting samples were sputter coated with 1 Au—Pd and examined with SEM.

The viability of cells on the nanofiber scaffolds were observed using LIVE/DEAD viability/cytotoxicity assay (Molecular Probes L-3224) or Cell/Tracker™ green probe (Molecular Probes (2-2925) (http://probes.invitrogen.com/servlets/publications?id=444). Cells were incubated on the nanofibers for at least 24 hours. Living cells were labeled with fluorescence and examined using a microscope. The viability of these cells was compared to those incubated on tissue culture dishes. Cells were collected from surfaces and resuspended. Cell suspensions were incubated at 37° C. with MTS solution for 3-4 hours in a 96-well plate. The absorbance at a wavelength of 570 nm was recorded in a microplate reader.

The adhesion of cells on the calcium phosphate nanofiber mat was compared using the percentage of remaining cells per unit area on the mat after removing loosely attached cells. The nanofiber scaffold was placed in culture plates. Fluorescence labeled cells (CellTracker) were added onto the nanofiber scaffolds and incubated for about 1 hour, depending on cell type. Unbound cells were removed by gentle rinsing with medium. Cells were imaged and the number of cells on the scaffolds counted.

The differentiation of osteoblast cells focuses on the analysis of the alkaline phosphatase ("ALP") activity, collagen synthesis and osteopontin and osteocalcin production. ALP activity was assessed by staining the cells on the nanofibers using a diazolim coupling reaction (Fast Blue RR Salt and naphthol AS-MX phosphate alkaline solution, Sigma, www.sigmaaldrich.com). Qualitative measurement of ALP activity was determined by analyzing the cell lysate. Cells were released from the surfaces with the trypsin/EDTA solution and lysed. Cell lysate was then incubated with p-nitrophenyl phosphate in an appropriate buffer (Sigma), and the ALP phosphatase activity was evaluated by monitoring the absorbance at 405 nm corresponding to the production of p-nitrophenol. Protein content was measured using BCA assay (Pierce, http://www.piercenet.com/products/browse.cfm?fldID=020201). The activity was expressed as n mlol of p-nitrophenol/min/mg/protein.

Collagen synthesis was detected using a histologic staining procedure (Mason's staining, Sigma). For quantitative comparison, hydroxyproline concentration was used to represent total collagen production using the method by Woessner (Woessner. *Arch. Biochem. Biophys.* 93: 440-447 (1961)). Samples were mixed with concentrated HCl and incubated at 110° C. for 16 hours. Hydroxyproline was oxidated with chloramine T solution and the Ehrlich's reagent (Sigma) added for color reaction. Absorbance was measured at 560 nm using a plate-reader.

Osteopontin and osteocalcin production were determined quantitatively using ELISA kits available from Assay Design and Zymed (www.invitrogen.com). The standard protocol provided by the manufacturer was followed.

Phenotypical expression of the cell lines isolated from the Immortomouse on each Ca—P nanofiber scaffold was analyzed at the mRNA level. Poly(A)-RNA was extracted using Microfastrack method (Invitrogen, www.invitrogen.com). The expression of mRNA for specific protein markers of the cell was determined.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill m the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. A nanofiber comprising calcium phosphate, wherein the calcium phosphate comprises a $Ca^{2+}$ ion and at least one phosphate ion having one or more Ca—O—P linkages selected from the group consisting of orthophosphate ($PO^{2-}$) ions, metaphosphate ($PO_4^{3-}$) ions, and pryophosphate ions ($P_2O_7^{4-}$), and optionally hydrogen or hydroxide ions, wherein the tensile strength of said nanofiber is between 25.0 and 1,000.0 MPa, wherein the nanofiber is electrospun nanofiber, and wherein the maximum distance between any two points on the outer surface of the nanofiber when seen in a cross-section to the longitudinal axis of the fiber is between 10.0 nm to 2.0 microns.

2. A nanofiber consisting essentially of calcium phosphate, wherein the calcium phosphate comprises a $Ca^{2+}$ ion and at least one phosphate ion having one or more Ca—O—P linkages selected from the group consisting of orthophosphate ($PO^{2-}$) ions, metaphosphate ($PO_4^{3-}$) ions, and pryophosphate ions ($P_2O_7^{4-}$), and optionally hydrogen or hydroxide ions, wherein the tensile strength of said nanofiber is between 25.0 and 1,000.0 MPa, wherein the nanofiber is electrospun nanofiber, and wherein the maximum distance between any two points on the outer surface of the nanofiber when seen in a cross-section to the longitudinal axis of the fiber is between 10.0 nm to 2.0 microns.

3. The nanofiber of claim 1 wherein the calcium phosphate is selected from the group consisting of tricalcium phosphate, dicalcium phosphate, calcium dihydrogen phosphate and hydroxyapatite.

4. The nanofiber of claim 1 wherein the calcium phosphate is non-derivatized.

5. The nanofiber of claim 1 wherein the nanofiber further comprises a polymer binder, wherein said polymer is selected from the group consisting of linear aliphatic polymers, water-soluble vinyl polymers and copolymers thereof.

6. The nanofiber of claim 5 wherein the water-soluble vinyl polymers are selected from the group consisting of polyvinyl alcohol, polyvinyl ether, polyvinyl pyrrolidone, polyvinyl acetate and copolymers thereof.

7. The nanofiber of claim 5 wherein the linear aliphatic polymers are selected from the group consisting of poly(glycolic acid), poly(lactic) acid and copolymers thereof.

8. The nanofiber of claim 5, wherein the copolymer is poly(lactic acid-co-glycolic acid).

9. The nanofiber of claim 5 wherein the linear aliphatic polymers are polyethers selected from the group consisting of polyethylene glycol, polyethylene oxide, polypropylene oxide, and copolymers thereof.

10. The nanofiber of claim 9, wherein the copolymer is poly(ethylene glycol-co-propylene oxide).

11. The nanofiber of claim 1, further comprising a polymer binder selected from the group consisting of poly(-caprolactone), poly(hydroxy butyrate), poly(propylene fumarate), tyrosine-derived polymers, segmented polyurethane-based polymers, polyphosphoesters, polyphosphazenes, polyanhydrides, poly(ortho esters) and copolymers thereof.

12. The nanofiber of claim 1, wherein the cross-section of said nanofiber to the longitudinal axis of the fiber is solid and comprises continuous calcium phosphate.

13. The nanofiber of claim 1, wherein the nanofiber when seen in any cross-section to the longitudinal axis of the fiber comprises a calcium phosphate shell surrounding a hollow core.

14. The nanofiber of claim 1, wherein the nanofiber when seen in any cross-section to the axis of the fiber comprises a calcium phosphate shell surrounding a solid core comprising at least one polymeric substance.

15. The nanofiber of claim 14, wherein the polymeric substance of the solid core is selected from the group consisting of biodegradable polymers.

16. The nanofiber of claim 15, wherein the polymeric substance of the solid core is an immiscible polymer that does not react or dissolve in ethanol.

17. The nanofiber of claim 15, wherein the polymer is selected from the group consisting of poly(glycolic acid), poly(lactic) acid, and poly(lactic acid-co-glycolic acid).

18. The nanofiber of claim 14, wherein the solid core further comprises a functional additive.

19. The nanofiber of claim 18, wherein the functional additive is a carbonate.

20. The nanofiber of claim 18, wherein the functional additive is a fluoride.

21. The nanofiber of claim 18, wherein the functional additive is selected from the group consisting of Sr, Mg, Mn, Zn, Na and K-based compounds.

22. The nanofiber of claim 18, wherein the functional additive is a biologically active material selected from the group consisting of proteins, peptides, nucleic acids, antibiotics, antimicrobials, anti-inflammatories, steroids and chemotherapeutic agents.

23. The nanofiber of claim 18, wherein the functional additive is a biologically active material selected from the group consisting of osteogenic factors, neurotrophic factors, bone morphogenic proteins, transforming growth factors, vascular endothelial growth factors, platelet-derived growth factors, neurotrophins and cytokines.

24. The nanofiber of claim 1, wherein the maximum distance between any two points on the outer surface of the nanofiber when seen in a cross-section to the longitudinal axis of the fiber is between 50.0 nm to 500.0 nm.

25. The nanofiber of claim 24, wherein the maximum distance between any two points on the outer surface of the nanofiber when seen in a cross-section to the longitudinal axis of the fiber is between 75.0 nm to 300.0 nm.

26. The nanofiber of claim 25, wherein the maximum distance between any two points on the outer surface of the nanofiber when seen in a cross-section to the longitudinal axis of the fiber is between 100.0 nm to 200.0 nm.

27. The nanofiber of claim 1, wherein the nanofiber comprises at least one internal pore.

28. The nanofiber of claim 27, wherein the diameter of the internal pore is between 0.1 nm to 10.0 nm.

29. The nanofiber of claim 28, wherein the size of the internal pore is between 2.0 nm to 5.0 nm.

30. The nanofiber of claim 27, wherein one or more of the internal pores are interconnected.

31. The nanofiber of claim 1, wherein the calcium phosphate in said nanofiber is crystalline.

32. The nanofiber of claim 1, wherein the degree of crystallinity of said nanofiber as measured by X-ray diffraction is at least 40%.

33. The nanofiber of claim 32, wherein the degree of crystallinity of said nanofiber as measured by X-ray diffraction is at least 60%.

34. The nanofiber of claim 33, wherein the degree of crystallinity of said nanofiber as measured by X-ray diffraction is between 70% and 99%.

35. The nanofiber of claim 1, wherein the elongational viscosity of said nanofiber is between 10.0 poise to 1,000.0 poise.

36. The nanofiber of claim 35, wherein the elongational viscosity of said nanofiber is between 200.0 poise to 600.0 poise.

37. The nanofiber of claim 1, wherein the surface charge of said nanofiber is between neutral to net positive.

38. A nanofiber matrix comprising a three-dimensional network of randomly-dispersed nanofibers, wherein each nanofiber is the nanofiber of claim 1, and a plurality of said nanofibers are in physical contact with one another so as to enclose one or more interconnected interstices between the nanofibers.

39. The nanofiber matrix of claim 38, wherein the interstices between the randomly-dispersed nanofibers are pores.

40. The nanofiber matrix of claim 39, wherein the cross-sectional dimensions of the pores range from 0.5 microns to 50.0 microns.

41. The nanofiber matrix of claim 40, wherein the cross-sectional dimensions of the pores range from 1.0 microns to 10.0 microns.

42. The nanofiber matrix of claim 38, wherein said nanofibers are randomly-dispersed to form a nanofiber mat.

43. The nanofiber matrix of claim 38, wherein said nanofibers are randomly-dispersed to form a nanofiber scaffold.

44. The nanofiber matrix of claim 38, wherein the specific surface area of the nanofiber matrix is greater than 10 $m^2/g$.

45. The nanofiber matrix of claim 44, wherein the specific surface area of the nanofiber matrix is between 100 $m^2/g$ and 1,200 $m^2/g$.

46. The nanofiber matrix of claim 45, wherein the specific surface area of the nanofiber matrix is between 600 $m^2/g$ and 1,100 $m^2/g$.

47. The nanofiber matrix of claim 46, wherein the specific surface area of the nanofiber matrix is between 800 $m^2/g$ and 1,000 $m^2/g$.

48. A method to synthesize a nanofiber matrix comprising a plurality of randomly-dispersed nanofibers of claim 1, comprising the steps of (i) sol-gel synthesizing a calcium phosphate sol-gel precursor in an aqueous solvent, (ii) electro-spinning said sol-gel precursor to form a plurality of nanofibers; and (iii) optionally, calcinating the nanofibers produced by the electro-spinning step.

49. A method to synthesize a nanofiber matrix comprising a plurality of randomly-dispersed nanofibers of claim 1, comprising the steps of (i) sol-gel synthesizing a calcium phosphate sol-gel precursor in an aqueous solvent, (ii) sol-gel synthesizing a polymeric substance sol-gel precursor in an aqueous solvent; (iii) co-axial electro-spinning the calcium phosphate sol-gel precursor with the polymeric substance sol-gel precursor such that each nanofiber comprises a calcium phosphate shell around a core comprising the polymeric substance; and (iv) optionally, calcinating the nanofiber produced by the electro-spinning step.

50. The method of claim 48 or 49, wherein the calcium phosphate precursor further comprises a polymer binder.

51. The method of claim 48 or 49, further comprising the step of calcinating the nanofiber produced by the electro-spinning step.

52. The method of claim 48 or 49, wherein sol-gel synthesis of the calcium phosphate sol-gel precursor comprises (a) hydrolyzing a phosphate-based material in an aqueous solvent; (b) adding a calcium-based material to the hydrolyzed phosphate-based material to form a calcium-phosphate sol-gel precursor solution; (c) optionally aging the calcium-phosphate sol-gel precursor solution for at least 16 hours; and (d) optionally adding a polymer binder to the calcium-phosphate solution.

53. The method of claim 52, wherein the calcium phosphate sol-gel precursor synthesized by said method is a polymer comprising a plurality of linearly-arranged oligomeric derivatives containing a Ca—O—P bond.

54. The method of claim 52 wherein the molecular weight of the calcium phosphate sol-gel precursor is between 10,000 amu and 300,000 amu.

55. The method of claim 54, wherein the molecular weight of the calcium phosphate sol-gel precursor is between 100,000 amu and 200,000 amu.

56. The method of claim 52, wherein the Calcium:Phosphate:water:solvent molar ratio is 1.67:1:3-6.5:7.4-14.8.

57. The method of claim 56 wherein the Calcium:Phosphate:water:solvent molar ratio is 1.67:1:6.5:14.8.

58. The method of claim 52, wherein the calcium-based material is selected from the group consisting of calcium nitrate, calcium acetate, calcium ethoxide and calcium glycolate.

59. The method of claim 52, wherein the phosphate-based material is selected from the group consisting of triethyl phosphate and phosphate ethers.

60. The method of claim 52, wherein the aqueous solvent comprise an alcohol.

61. The method of claim 60, wherein the alcohol is ethanol.

62. The method of claim 52, wherein the polymer binder is selected from the group consisting of polyvinyl alcohols, polyglycolic acids and copolymers thereof.

63. The method of claim 62, wherein the polymer binder is added in the form of a 10% by weight aqueous solution.

64. The method of claim 63, wherein the 10% by weight polymer binder aqueous solution is mixed with the calcium phosphate sol-gel precursor at a volumetric ratio between 1.5 to 4.5.

65. The method of claim 49, wherein the core-forming polymeric substance comprises a biodegradable polymer.

66. The method of claim 65, wherein the biodegradable polymer is an immiscible polymer that does not react or dissolve in ethanol.

67. The method of claim 66, wherein the polymer is selected from the group consisting of pyridine, poly(glycolic acid), poly(lactic) acid and poly(lactic acid-co-glycolic acid).

68. The method of claim 66, wherein the polymer is selected from the group consisting of silica-based compounds.

69. The method of claim 68, wherein the silica-based compound is tetraethyl orthosilicate (TEOS).

70. The method of claim 49 wherein the sol-gel synthesis of the polymeric substance precursor comprises (a) catalytically hydrolyzing the polymer in an aqueous solvent; (b) heating the reaction product of step (a) such that the sol-gel synthesized polymer precursor comprises at least one linear chain of oligomer derivatives.

71. The method of claim 48 or 49, wherein the calcination step comprises heating the electrospun fibers to a temperature greater than 350° C.

72. The method of claim 71, wherein the calcination step comprises heating the electrospun fibers to a temperature of between 500° C. to 1,200° C.

73. The method of claim 72, wherein the calcination step comprises heating the electrospun fibers to a temperature of between 600° C. to 800° C.

74. The method of claim 48 or 49, wherein the calcination step comprises heating the electrospun fibers for between two and twelve hours.

75. The method of claim 74, wherein the calcination step comprises heating the electrospun fibers for between five to seven hours.

76. The method of claim 48 or 49, further comprising evaporating the aqueous solvent.

77. A method of culturing bone cells on a nanofiber matrix comprising the nanofiber of claim 1, wherein the nanofiber matrix is placed in a cell-culture medium and the bone cells allowed to adhere to the nanofiber matrix.

78. The method of claim 77, wherein the bone cells are osteoblasts.

79. A method of culturing dental cells on a nanofiber matrix comprising the nanofiber of claim 1, wherein the nanofiber matrix is placed in a cell-culture medium, and the dental cells allowed to adhere to the nanofiber matrix.

80. The method of claim 79, wherein the dental cells are odontoblasts.

81. A method of repairing mammalian bone tissue comprising the steps of (i) culturing bone cells on a nanofiber matrix comprising the nanofiber of claim 1, wherein the nanofiber matrix is placed in a cell-culture medium and the bone cells allowed to adhere to the nanofiber matrix; and (ii) placing said nanofiber matrix adjacent to the bone tissue needing repair.

82. A method of regenerating mammalian bone tissue comprising the steps of (i) culturing bone cells on a nanofiber matrix comprising the nanofiber of claim 1, wherein the nanofiber matrix is placed in a cell-culture medium and the bone cells allowed to adhere to the nanofiber matrix; and (ii) placing said nanofiber matrix adjacent to the bone tissue needing regeneration.

83. A method of repairing mammalian dental structures comprising the steps of (i) culturing dental cells on a nanofiber matrix comprising the nanofiber of claim 1, wherein the nanofiber matrix is placed in a cell-culture medium and the dental cells allowed to adhere to the nanofiber matrix; and (ii) placing said nanofiber matrix adjacent to the dental structure needing repair.

84. A method of regenerating mammalian dental structures comprising the steps of (i) culturing dental cells on a nanofiber matrix comprising the nanofiber of claim 1, wherein the nanofiber matrix is placed in a cell-culture medium and the dental cells allowed to adhere to the nanofiber matrix; and (ii) placing said nanofiber matrix adjacent to the dental structure needing regeneration.

85. A method of reconstructing an injured ligament in between a hard bone and a soft tendon tissue, comprising the step of placing a nanofiber matrix comprising the nanofibers of claim 1 onto the surface of a soft tendon tissue and adjacent to the injured ligament, such that bone cells can adhere to the nanofiber matrix and proliferate to bone tissue like densities thereby allowing the tendon to connect to the hard bone via said nanofiber matrix, wherein the nanofiber matrix is optionally pre-cultured with bone cells.

* * * * *